(12) United States Patent
Chavarria et al.

(10) Patent No.: US 11,633,285 B2
(45) Date of Patent: *Apr. 25, 2023

(54) MODIFIED GLENOID COMPONENTS AND METHODS OF INSTALLING SAME

(71) Applicant: DEPUY SYNTHES PRODUCTS, INC., Raynham, MA (US)

(72) Inventors: Jason M. Chavarria, Warsaw, IN (US); Kyle E. Lappin, Fort Wayne, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 14 days.

This patent is subject to a terminal disclaimer.

(21) Appl. No.: 16/922,912

(22) Filed: Jul. 7, 2020

(65) Prior Publication Data

US 2020/0330237 A1    Oct. 22, 2020

Related U.S. Application Data

(63) Continuation of application No. 14/853,618, filed on Sep. 14, 2015, now Pat. No. 10,702,390, which is a
(Continued)

(51) Int. Cl.
*A61F 2/40* (2006.01)
*A61B 17/16* (2006.01)
*A61F 2/30* (2006.01)

(52) U.S. Cl.
CPC ........ *A61F 2/4081* (2013.01); *A61B 17/1604* (2013.01); *A61B 17/1684* (2013.01);
(Continued)

(58) Field of Classification Search
CPC .. A61F 2002/30878; A61F 2002/30881; A61F 2002/30884; A61F 2002/30891; A61F 2/4081

See application file for complete search history.

(56) References Cited

U.S. PATENT DOCUMENTS 4,349,336 A    9/1982  Weissman
4,608,053 A    8/1986  Keller
(Continued)

FOREIGN PATENT DOCUMENTS

CN    102302375 A    1/2012
EP    1323395 A2    7/2003
(Continued)

OTHER PUBLICATIONS

Office Action and English Translation for Chinese Patent Application No. 201310268086.1, dated Mar. 2, 2016, 11 pages.
(Continued)

*Primary Examiner* — Christopher D. Prone
(74) *Attorney, Agent, or Firm* — Barnes & Thornburg LLP (57) ABSTRACT

A glenoid component for securement to a glenoid surface of a scapula comprises a body portion having a first surface adapted to contact the glenoid surface of a scapula and a second surface configured to receive the head portion of a humerus. The glenoid component further includes an anchor peg for penetrating the glenoid surface of the scapula so as to secure the body portion to the glenoid surface of the scapula. The anchor peg includes a cylindrical shaft extending from the first surface of the body portion and a fin secured to and extending outwardly from the cylindrical shaft. The glenoid component further includes a feature that prevents rotation of the glenoid component.

7 Claims, 13 Drawing Sheets

Related U.S. Application Data continuation of application No. 13/790,633, filed on Mar. 8, 2013, now abandoned.

(60) Provisional application No. 61/665,633, filed on Jun. 28, 2012.

(52) U.S. Cl.
CPC .............. *A61F 2002/30113* (2013.01); *A61F 2002/30154* (2013.01); *A61F 2002/30571* (2013.01); *A61F 2002/30878* (2013.01); *A61F 2002/30881* (2013.01); *A61F 2002/30884* (2013.01); *A61F 2002/30891* (2013.01)

(56) References Cited

U.S. PATENT DOCUMENTS

| | | |
|---|---|---|
| 4,725,280 A | 2/1988 | Laure |
| 5,571,203 A | 11/1996 | Masini |
| 6,334,874 B1 | 1/2002 | Tornier et al. |
| 6,699,289 B2 | 3/2004 | Iannotti et al. |
| 6,783,549 B1 | 8/2004 | Stone et al. |
| 6,911,047 B2 | 6/2005 | Rockwood, Jr. et al. |
| 7,160,328 B2 | 1/2007 | Rockwood, Jr. et al. |
| 10,702,390 B2 | 7/2020 | Chavarria et al. |
| 2004/0225367 A1 | 11/2004 | Glien et al. |
| 2005/0060039 A1 | 3/2005 | Cyprien |
| 2005/0209700 A1 | 9/2005 | Rockwood et al. |
| 2005/0261775 A1 | 11/2005 | Baum et al. |
| 2006/0069443 A1 | 3/2006 | Deffenbaugh et al. |
| 2007/0219637 A1 | 9/2007 | Berelsman et al. |
| 2008/0147203 A1 | 6/2008 | Cronin et al. |
| 2009/0192621 A1 | 7/2009 | Winslow et al. |
| 2010/0016972 A1 | 1/2010 | Jansen et al. |
| 2010/0228352 A1* | 9/2010 | Courtney, Jr. ........ A61F 2/4081 606/301 |
| 2010/0268238 A1 | 10/2010 | Sikora et al. |
| 2011/0029089 A1 | 2/2011 | Giuliani et al. |
| 2013/0144393 A1* | 6/2013 | Mutchler .............. A61F 2/4081 623/19.11 |

FOREIGN PATENT DOCUMENTS

| | | |
|---|---|---|
| FR | 2743295 A1 | 7/1997 |
| JP | 2001293019 A | 10/2001 |
| JP | 2002516695 A | 6/2002 |
| JP | 2005511243 A | 4/2005 |
| JP | 6173793 B2 | 8/2017 |
| WO | 2011073169 A1 | 6/2011 |

OTHER PUBLICATIONS

Japanese Office Action and English language translation of Japanese Office Action, Japanese Application No. 2017-131775, dated Apr. 16, 2019, 6 pages.

English translation of Third Office Action issued by the State Intellectual Property Office of the People's Republic of China, Chinese Application No. 2013102680861, dated Apr. 14, 2017, 8 pages.

Japanese Office Action and English language translation of Japanese Office Action, Japanese Application No. 2013-135018, dated Dec. 13, 2016, 5 pages.

European Search Report issued in connection with European Patent Application No. 13174071.4, dated Sep. 30, 2013.

\* cited by examiner

MODIFIED GLENOID COMPONENTS AND METHODS OF INSTALLING SAME

CROSS-REFERENCE TO RELATED U.S. PATENT APPLICATION

This application claims priority under 35 U.S.C. § 120 to U.S. patent application Ser. No. 14/853,618, entitled "MODIFIED GLENOID COMPONENTS AND METHODS OF INSTALLING SAME," which was filed on Sep. 14, 2015, now issued as U.S. Pat. No. 10,702,390, which claims priority under 35 U.S.C. § 120 to U.S. patent application Ser. No. 13/790,633, entitled "MODIFIED GLENOID COMPONENTS AND METHODS OF INSTALLING SAME," which was filed on Mar. 8, 2013, which claims priority under 35 U.S.C. § 119 to U.S. Patent Application No. 61/665,633, entitled "MODIFIED GLENOID COMPONENTS AND METHODS OF INSTALLING SAME," which was filed on Jun. 28, 2012. The disclosure of each above-noted application is incorporated herein by reference.

TECHNICAL FIELD

The present disclosure relates generally to a glenoid component, and more particularly, to a glenoid component that resists rotation and pullout and a method of implanting the glenoid component.

BACKGROUND

During the lifetime of a patient, it may be necessary to perform a total shoulder replacement procedure on the patient as a result of, for example, disease or trauma. In a total shoulder replacement procedure, a humeral component having a head is utilized to replace the natural head of the arm bone or humerus. The humeral component typically has an elongated intramedullary stem that is utilized to secure the humeral component to the patient's humerus. In such a total shoulder replacement procedure, the natural glenoid surface of the scapula is resurfaced or otherwise replaced with a glenoid component which provides a bearing surface for the head of the humeral component.

Glenoid components generally include a body that defines a bearing surface for receiving the head of the humeral component and a number of attachment pegs integrally formed with the body. The attachment pegs are inserted and thereafter secured into a corresponding number of holes that are drilled in the glenoid surface of the scapula by use of bone cement. The pegs prevent rotation of the glenoid component.

SUMMARY

According to an illustrative embodiment, a glenoid component for securement to a glenoid surface of a scapula so as to provide a bearing surface for a head portion of a humerus comprises a body portion and an anchor peg. The body portion includes a first surface adapted to contact the glenoid surface of a scapula and a second surface configured to receive the head portion of the humerus. The anchor peg is for penetrating the glenoid surface of the scapula so as to secure the body portion to the glenoid surface of the scapula. The anchor peg includes a cylindrical shaft extending from the first surface of the body portion and a fin secured to and extending outwardly from the cylindrical shaft, the fin being generally square-shaped.

The glenoid component includes a plurality of generally square-shaped fins secured to and extending outwardly from the cylindrical shaft of the anchor peg.

The fins are generally square-shaped and have rounded corners.

The anchor peg is adapted for insertion into a hole within a glenoid surface of a scapula and the fins have a width that is greater than a width or diameter of a hole in which the anchor peg is inserted. The fins are configured to prevent rotation of the glenoid component within the glenoid surface.

Side edges of the fins are configured to have an interference with a wall forming a hole in which the anchor peg is inserted of between about 0.25 millimeters and about 2 millimeters.

Rounded corners of the fins are configured to have an interference with the wall forming the hole in which the anchor peg is inserted of between about 0.5 millimeters and about 3 millimeters. The interference between the side walls and the rounded corners with the wall forming the hole prevent rotation of the glenoid component.

The anchor peg is configured for insertion into a generally square-shaped hole in the glenoid surface of the scapula.

According to a further illustrative embodiment, a glenoid component for securement to a glenoid surface of a scapula so as to provide a bearing surface for a head portion of a humerus comprises a body portion, an anchor peg, and at least one gusset. The body portion includes a first surface adapted to contact the glenoid surface of a scapula and a second surface configured to receive the head portion of the humerus. The anchor peg is for penetrating the glenoid surface of the scapula so as to secure the body portion to the glenoid surface of the scapula. The anchor peg includes a cylindrical shaft extending from the first surface of the body portion and a fin secured to and extending outwardly from the cylindrical shaft. The at least one gusset is secured to and extending downwardly from the first surface of the body portion and secured to and extending outwardly from the cylindrical shaft of the anchor peg.

An angled edge is formed by the gusset and extends between the first surface of the body portion and the anchor peg.

The angled edge of the gusset is configured to be driven into the glenoid surface of the scapula to prevent rotation of the glenoid component.

The glenoid component includes a plurality of gussets secured to and extending downwardly from the first surface of the body portion and secured to and extending outwardly from the cylindrical shaft of the anchor peg.

The gussets are orthogonal to the first surface of the body portion and the cylindrical shaft of the anchor peg.

Four gussets are spaced about a longitudinal axis of the anchor peg with about ninety degrees between adjacent gussets.

The gussets are configured to be driven into the glenoid surface of the scapula to prevent rotation of the glenoid component.

According to another illustrative embodiment, a glenoid component for securement to a glenoid surface of a scapula so as to provide a bearing surface for a head portion of a humerus comprises a body portion and an anchor peg. The body portion includes a first surface adapted to contact the glenoid surface of a scapula and a second surface configured to receive the head portion of the humerus. The anchor peg is for penetrating the glenoid surface of the scapula so as to secure the body portion to the glenoid surface of the scapula. The anchor peg includes a cylindrical shaft extending from the first surface of the body portion and a fin secured to and extending outwardly from the cylindrical shaft. The fin includes at least one cutout configured to allow the fin to deflect outwardly along a hole in which the glenoid component is secured, thereby preventing rotation of the glenoid component.

The fin includes first and second opposing cutouts, wherein each of the cutouts includes a first leg and a second leg forming generally triangular cutouts.

The cutouts are symmetrical about an axis that bisects the fins.

The body portion of the glenoid component is generally circular.

Other aspects and advantages of the present disclosure will become apparent upon consideration of the following drawings and detailed description, wherein similar structures have similar reference numbers.

BRIEF DESCRIPTION OF THE DRAWINGS

The detailed description particularly refers to the following figures, in which.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Figure 1:
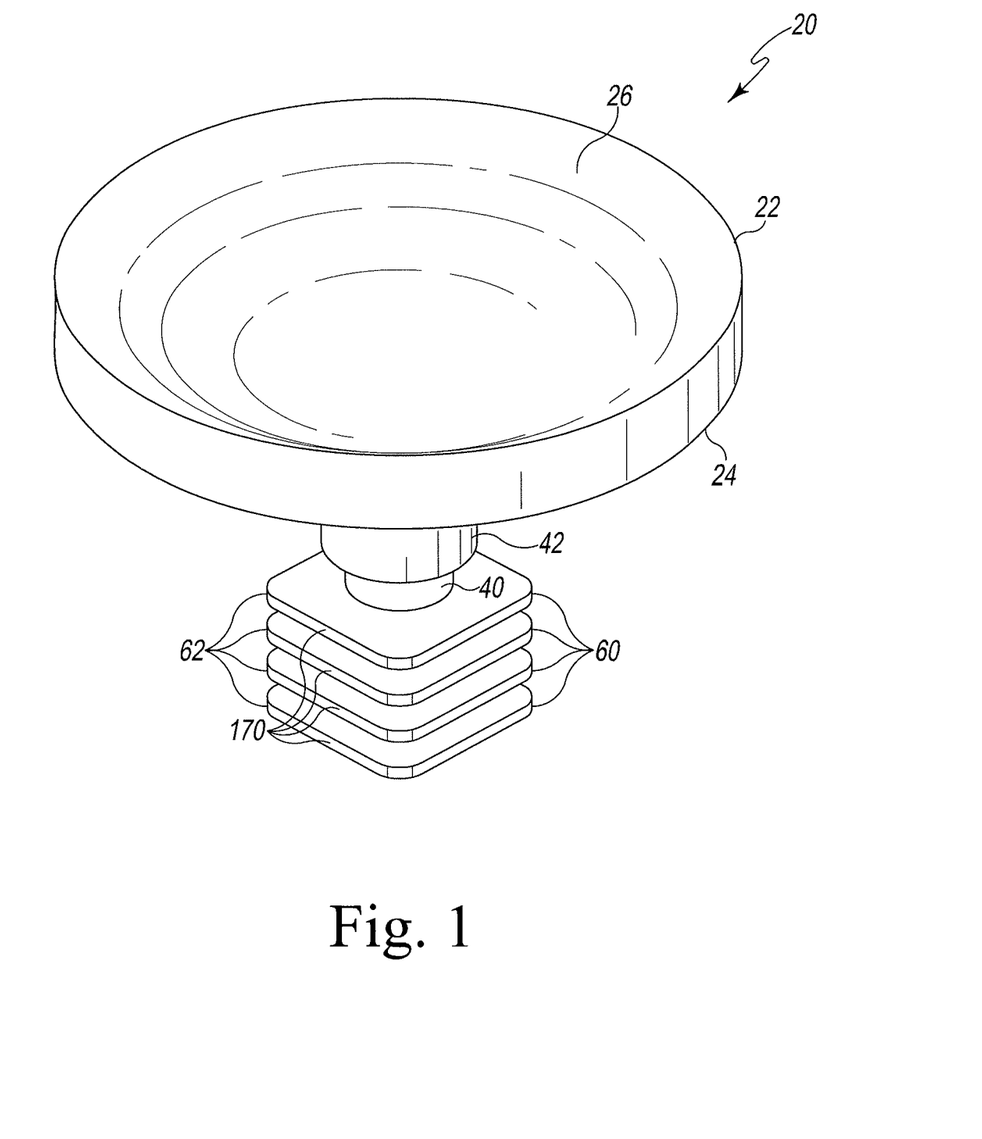
FIG. 1 is a top perspective view of a first embodiment of a glenoid component.
Figure 2:
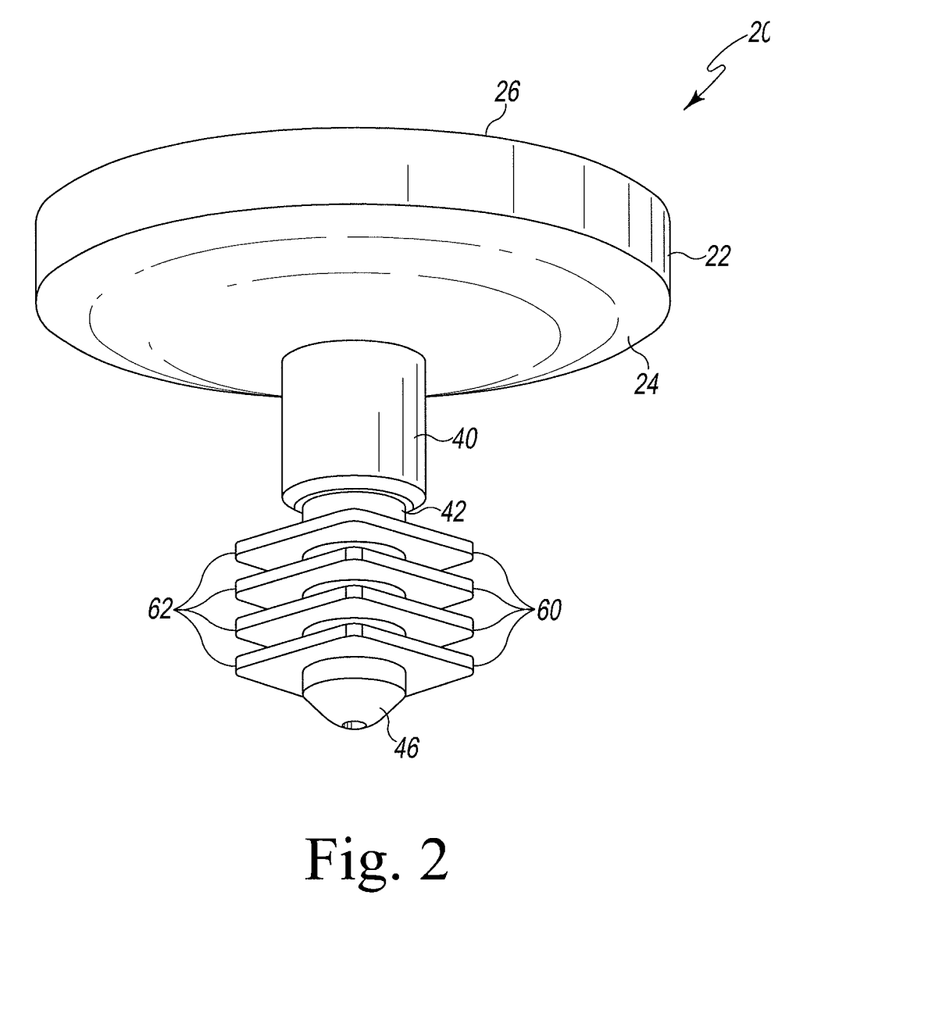
FIG. 2 is a bottom perspective view of the glenoid component of FIG. 1.

Referring now to the figures, a first embodiment of a polymer glenoid component 20 is depicted in FIGS. 1 and 2. The glenoid component 20 includes a body 22 having a generally convex surface 24 and a generally concave surface 26 opposite the convex surface 24. The convex surface 24 generally abuts or otherwise contacts at least a portion of the glenoid surface of the scapula. The body 22 of the glenoid component 20 generally has a shaped that is generally circular, such that the concave surface 26 generally forms a spherical surface. In this manner, the concave surface 26 of the body 22 provides a smooth bearing surface upon which the head 28 articulates and which generally matches the shape of the spherical head 28.

Figure 8:
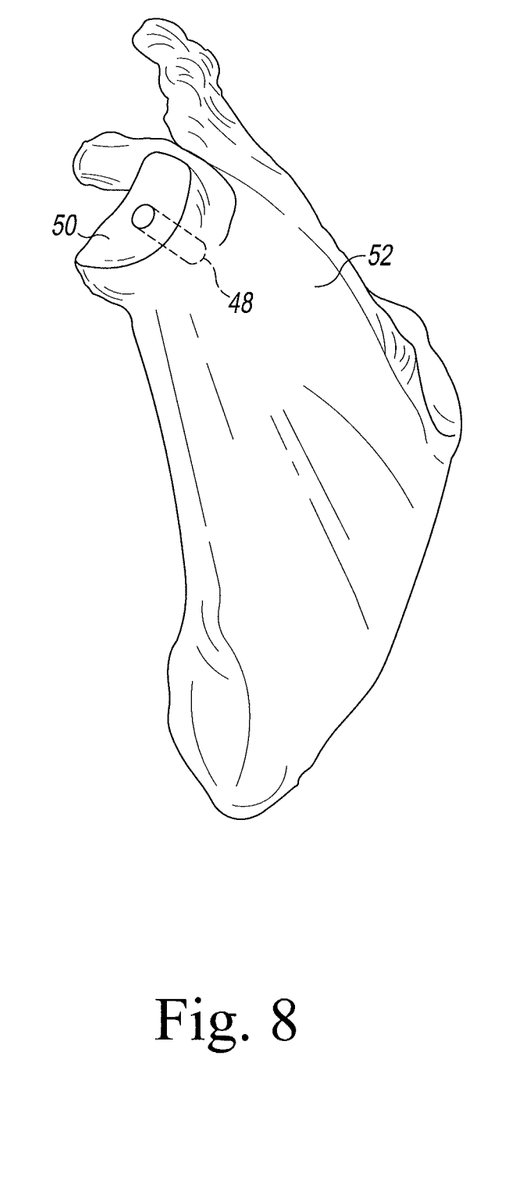
FIG. 8 is a perspective view depicting a glenoid surface of a scapula with a hole for securing a glenoid component to the glenoid surface.
Figure 9:
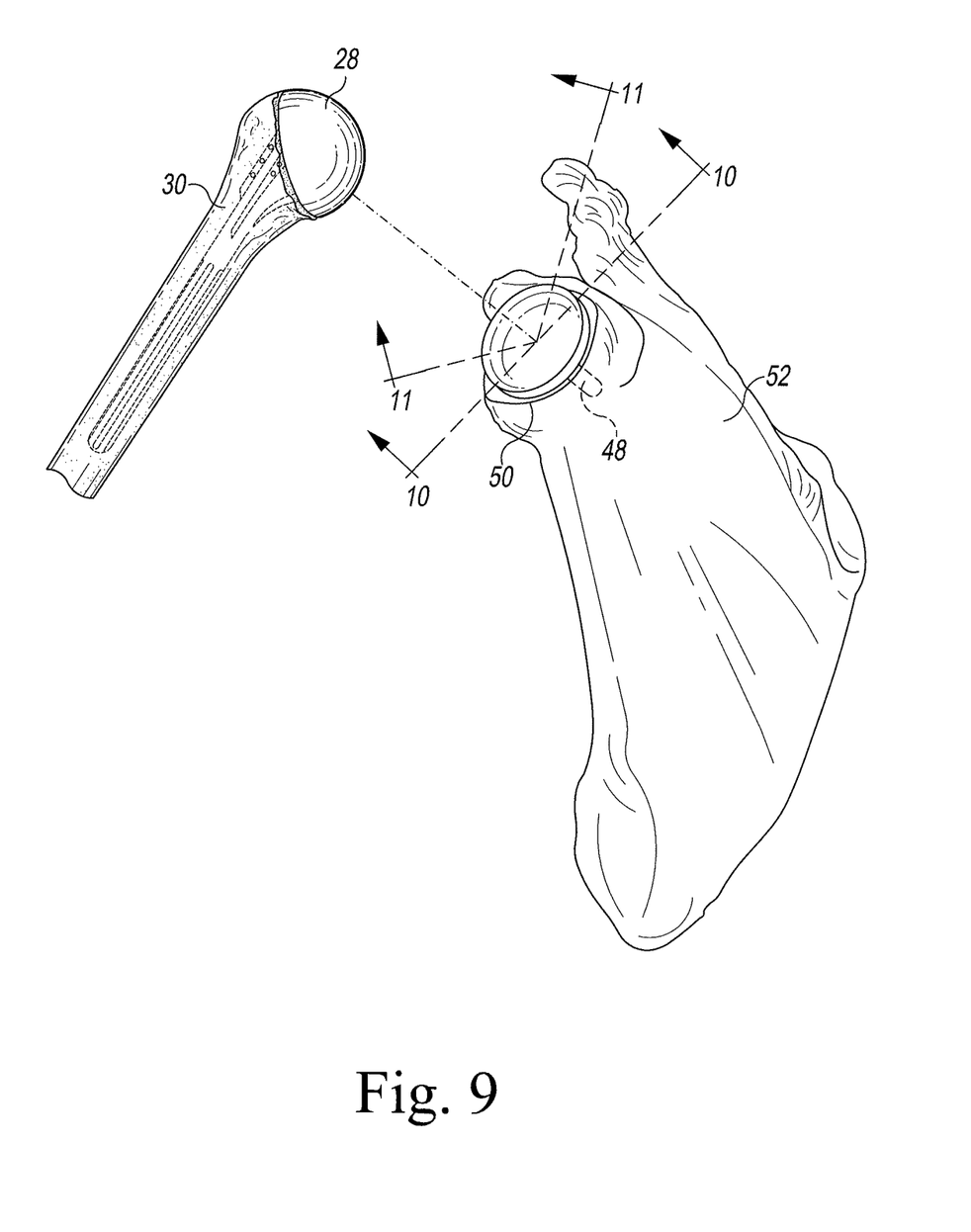
FIG. 9 is a partial exploded perspective view depicting the glenoid component of FIG. 1 secured within the glenoid surface of FIG. 8 and further showing a humeral component.

The glenoid component 20 also includes an anchor peg 40 secured to and extending generally orthogonal to the convex surface 24 of the body 22. As shown in FIGS. 1 and 2, the anchor peg 40 includes a cylindrical shaft 42 and a tapered head 46 at an end of the cylindrical shaft 42 that functions as a lead-in to facilitate insertion into a hole 48 drilled or otherwise formed in a glenoid surface 50 (as shown in FIGS. 8 and 9) of a patient's scapula 52. The anchor peg 40 may include a first cylindrical shaft segment extending from the convex surface 24 and having a first diameter and a second cylindrical shaft segment extending from the first cylindrical shaft segment and having a second diameter less than the first diameter, as seen in FIGS. 1 and 2. Alternatively, the anchor peg 40 may have a single diameter throughout a length of the cylindrical shaft 42.

The anchor peg 40 further includes a plurality of flexible radial fins 60 extending outwardly from an end 62 of the anchor peg 40. The fins 60 function to secure the glenoid component 20 within the glenoid surface 50. In addition, the flexible and deformable nature of the radial fins 60 extending from the anchor peg 40 allow the fins 60 to deform upon insertion of the anchor peg 40 into the hole 48, thereby creating resistance to extraction of the anchor peg 40 from the hole 48 once fully inserted therein.

The fins 60 of glenoid component 20, as best seen in FIGS. 1 and 2, are generally square-shaped with rounded corners 62. The fins 60 have a size and shape that creates an interference with walls forming the hole 48 that prevents easy removal of the glenoid component 20 from the glenoid surface 50 and prevents rotation of the glenoid component 20 without the use of a stabilizing peg, as will be discussed in greater detail hereinafter.

Figure 3:
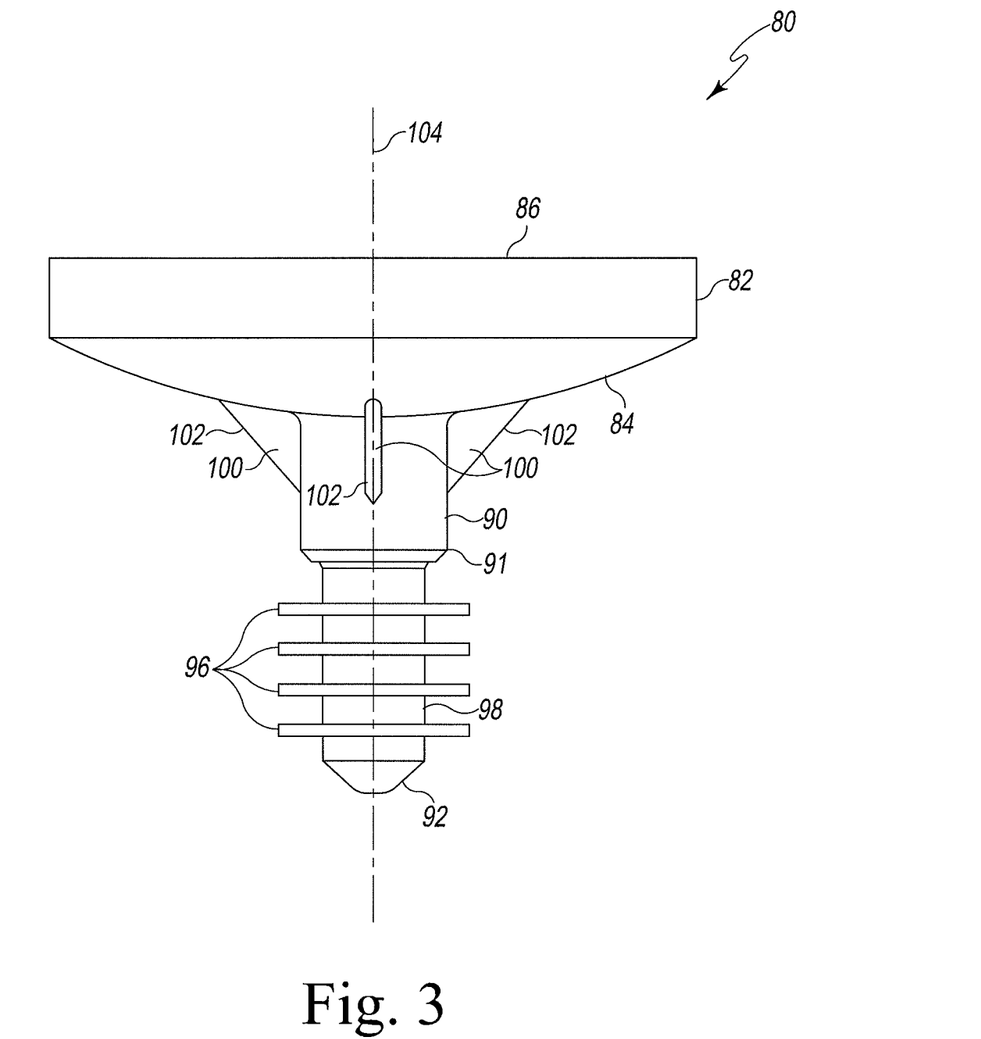
FIG. 3 is a side elevational view of a second embodiment of a glenoid component.
Figure 4:
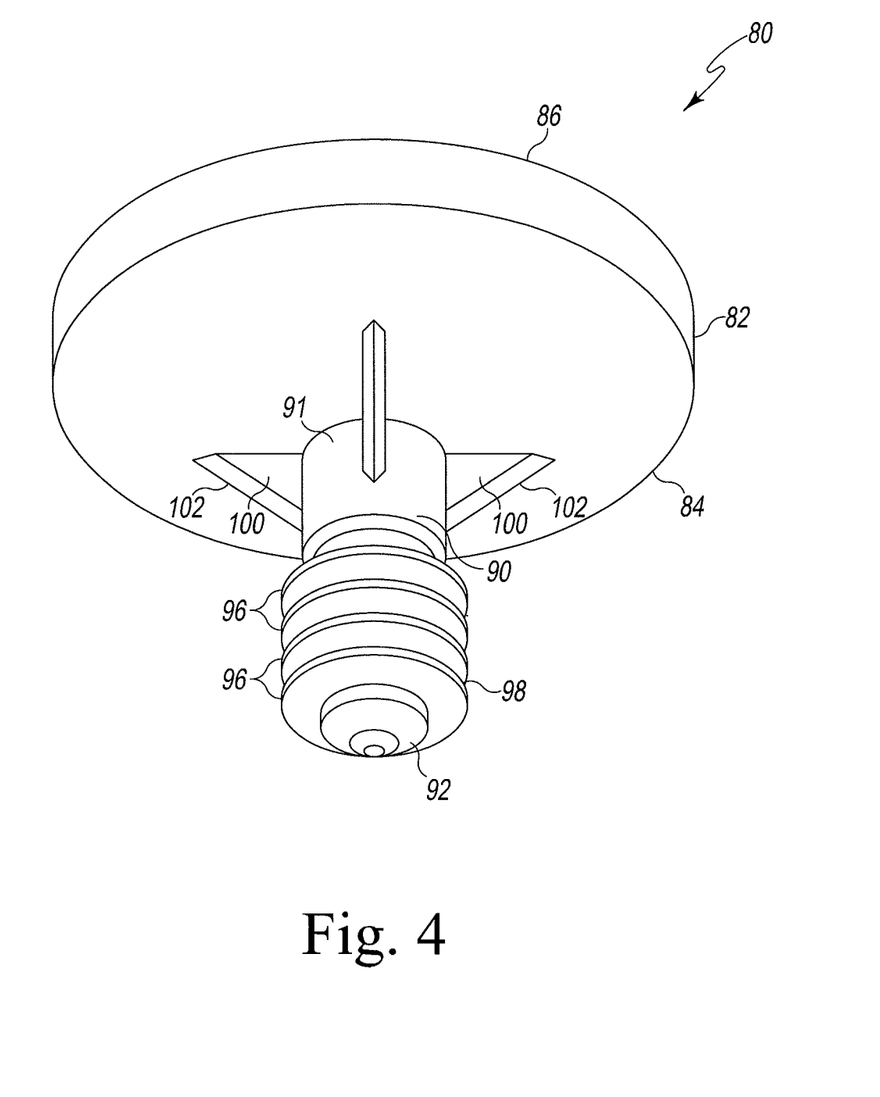
FIG. 4 is a bottom perspective view of the glenoid component of FIG. 3.

A second embodiment of a glenoid component 80 is depicted in FIGS. 3 and 4. The glenoid component 80 is similar to the glenoid component 20 of FIGS. 1 and 2 in that it includes a body 82 with opposing generally convex and generally concave surfaces 84, 86. The glenoid component 20 also includes an anchor peg 90 with a cylindrical shaft 91 and a tapered end 92. One manner in which the glenoid component 80 is different from the glenoid component 20 of the first embodiment is that it includes a plurality of generally circular fins 96 extending outwardly from an end 98 of the anchor peg 90.

Referring again to FIGS. 3 and 4, the glenoid component 80 further includes a plurality of gussets 100 extending downwardly from the convex surface 84 and outwardly from the anchor peg 90 adjacent the convex surface 84 of the body 82. The gussets 100 are also generally orthogonal to the convex surface 84 and the anchor peg 90 and extend outwardly from the peg 90 a distance greater than the fins 96 extend from the peg 90. An outer angled edge 102 of each gusset 100 extends between and is integrally attached to the convex surface 84 and the anchor peg 90. The gussets are spaced about a longitudinal axis 104 of the anchor peg 90 with about ninety degrees between adjacent gussets 100.

When the glenoid component 80 is installed within the glenoid surface 50, the gussets 100 are pressed into the glenoid surface 50 surrounding the anchor peg 90 and below the convex surface 84 of the body 82, thereby preventing rotation of the glenoid component 80 without the use of a stabilizing peg. Installation and functionality of the glenoid component will be discuss in greater detail below with respect to FIG. 13.

While four gussets 100 are depicted with respect to the embodiment of the glenoid component 80 of FIGS. 3 and 4, one or more gussets 100 may be utilized. In one embodiment, a single gusset 100 may be utilized. In another embodiment, eight gussets 100 may be utilized. The number of gussets 100 utilized may be determined based on the ability of those gussets 100 to prevent rotation of the glenoid component 80, the cost of additional gussets 100, and/or other factors.

Figure 5:
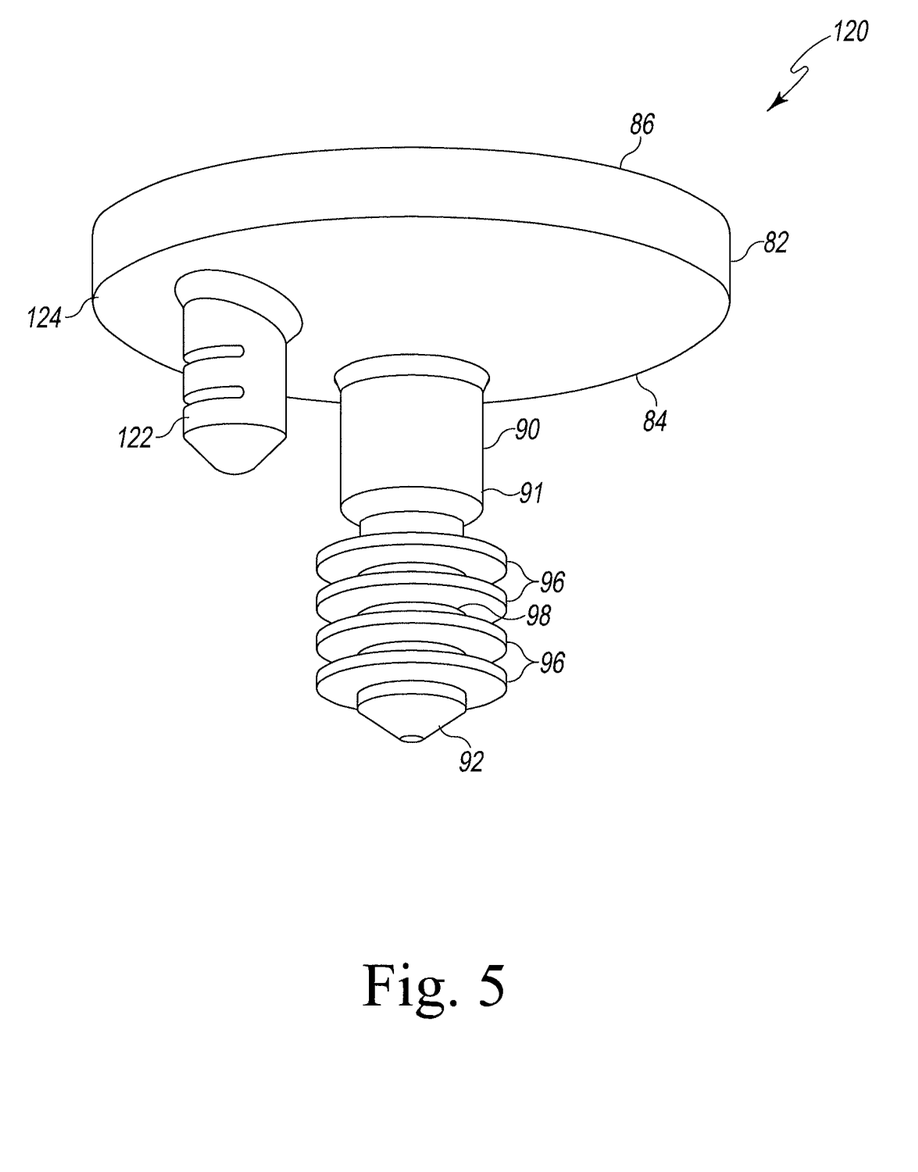
FIG. 5 is a bottom perspective view of a third embodiment of a glenoid component.

A third embodiment of a glenoid component 120 is shown in FIG. 5. The glenoid component 120 is similar to the glenoid component 80 of FIGS. 3 and 4 and, thus, similar features will be numbered similarly. The main difference is that the glenoid component 120 does not include gussets, but rather, includes a stabilizing peg 122 extending outwardly from the convex surface 84. The stabilizing peg 122 is spaced between the anchor peg 90 and an outer edge 124 of the body 82. While one stabilizing peg 122 is shown, other stabilizing pegs 122 may be spaced about the convex surface 84.

The stabilizing peg 122 prevents the body 82 of the glenoid component 120 from moving a plane perpendicular to the anchor peg 90 and prevent rotational movement of the glenoid component 120. Generally, the stabilizing peg 122 is shorter than the anchor peg 90. Moreover, if multiple stabilizing pegs 122 are utilized, one or more of the stabilizing pegs 122 may be shorter than the others, although other configurations may be used.

While the body 82, the anchor peg 90, and the stabilizing peg 122 of the glenoid component 120 are shown as being integral, one or more of the anchor peg 90 or stabilizing peg 122 may be separately secured to the body 82. As one skilled in the art would understand, any number of anchor pegs 90 or stabilizing pegs 122 may be utilized, the anchor peg 90 may include any features that aid in inserting the anchor peg 90 into a hole or retaining the anchor peg 90 within a hole, and/or the placement of the anchor peg(s) 90 and/or stabilizing peg(s) 122 may be modified without departing from the scope of the present disclosure.

In the embodiment of FIG. 5, one or more secondary holes (not shown) would be formed within the glenoid surface 50 and spaced between the hole 48 and an outer edge of the glenoid surface 50. The secondary holes may have a size and shape that conforms to the stabilizing peg(s) 122.

Figure 6:
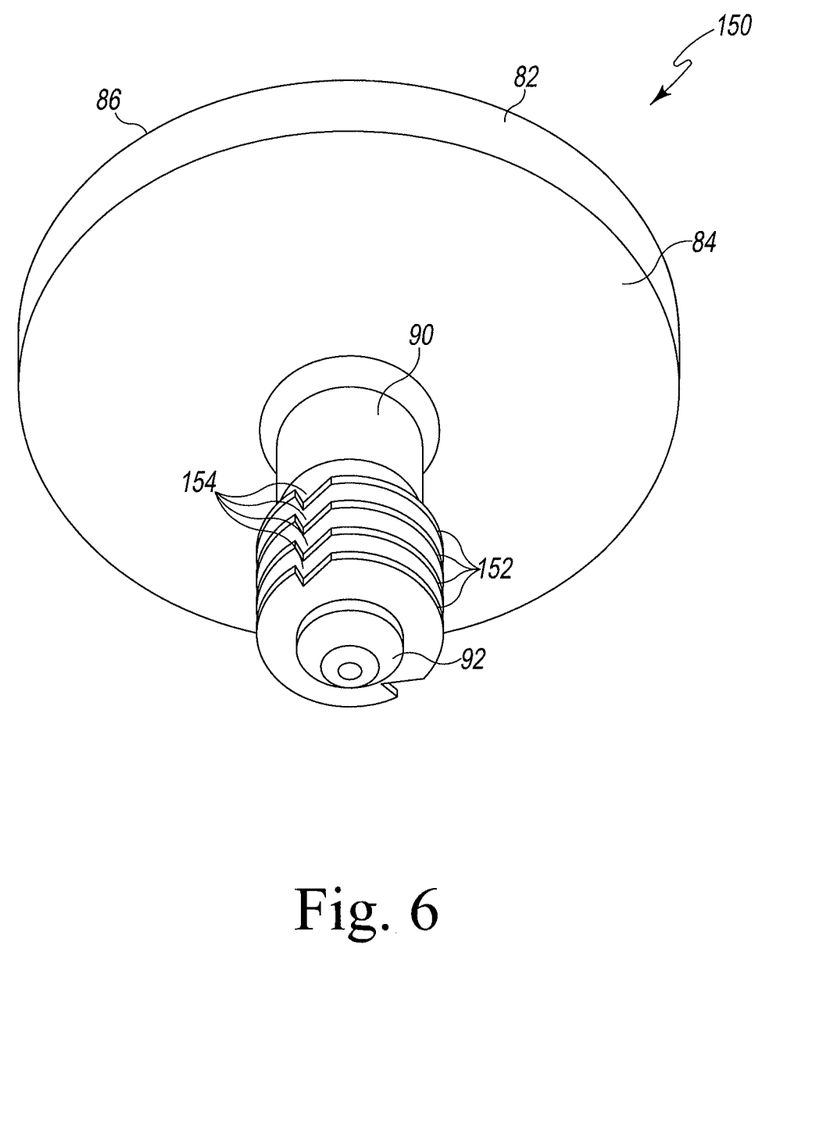
FIG. 6 is a bottom perspective view of a fourth embodiment of a glenoid component.

A fourth embodiment of a glenoid component 150 is depicted in FIG. 6. The glenoid component 150 is similar to the glenoid component 80 of FIGS. 3 and 4. In particular, the glenoid component 150 includes a similar body 82 with convex and concave surfaces 84, 86 and an anchor peg 90 having a cylindrical shaft 91 and a tapered end 92 and extending outwardly and transversely to the convex surface 84. The glenoid component 150 further includes a plurality of fins 152 extending outwardly from an end of the anchor peg 90. Upon insert of the anchor peg 90 into the hole 48, portions of the fins 152 deflect outwardly (toward an opening of the hole 48), thereby preventing rotation of the glenoid component 150 without the use of a stabilizing peg.

Figure 7:
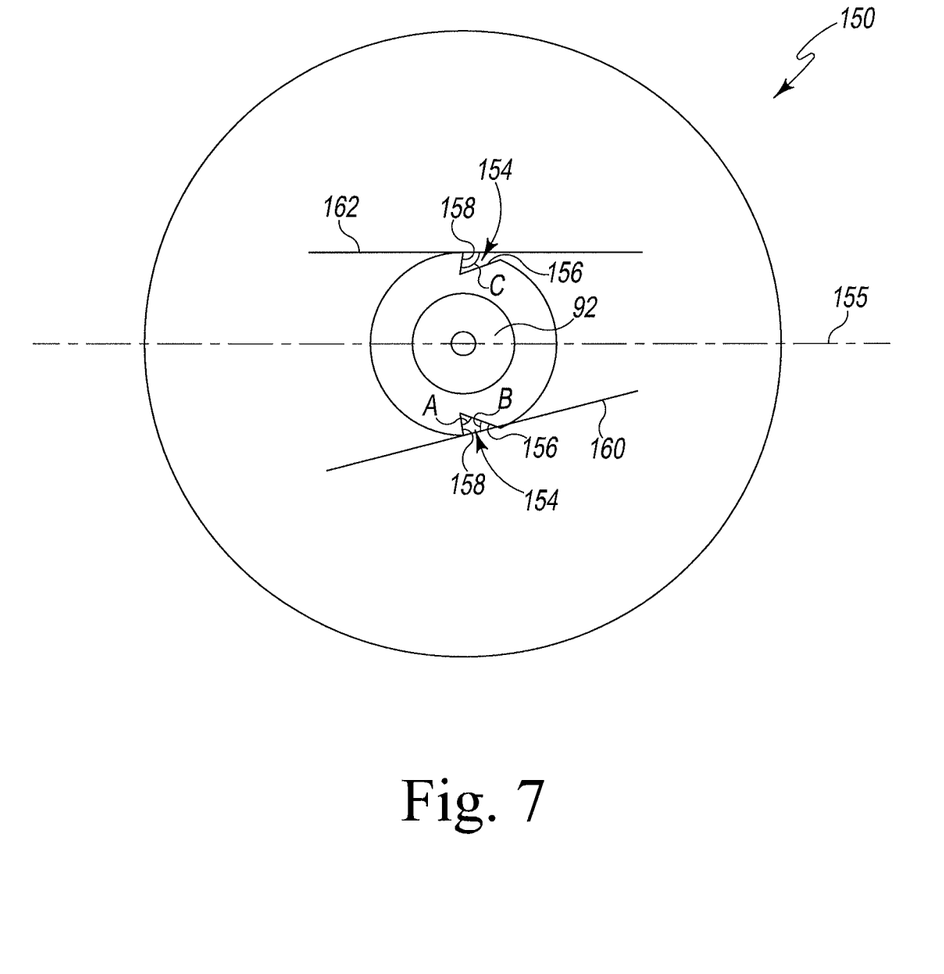
FIG. 7 is a bottom elevational view of the glenoid component of FIG. 6 and showing a shape of fins that extend outwardly from an anchor peg of the glenoid component.

Each of the fins 152 is generally disc-shaped and includes two opposing cutouts 154. The cutouts 154 are generally triangular in shape and are generally symmetrical about an axis 155 that bisects the fins 152. Optionally, the cutouts 154 may be asymmetrical. Each cutout 154 includes first and second legs 156, 158 that extend at an angle A with respect to one another. The first leg 156 of each cutout 154 extends at an angle B with respect to a line 160 tangent to an outer end of the first leg 156 and the second leg 158 of each cutout 154 extends at an angle C with respect to a line 162 tangent to an outer end of the second leg 158. Optionally, the cutouts 154 may be formed of another shape, for example, square-shaped or U-shaped. The cutouts 154 allow bone to grow between the fins 152 in two planes. While two cutouts 154 are depicted, any number of cutouts 154 is possible.

The glenoid components shown and described herein may be made of a polymeric material, for example, a polyethylene. One example of a suitable polyethylene is ultrahigh molecular weight polyethylene (UHMWPE). In addition to polymers, the glenoid components may be made from ceramic, metal, or a composite material. Examples of these materials include alumina, zirconia, and alumina/zirconia composite or composite material.

A method of securing the glenoid component 20 of FIGS. 1 and 2 to the glenoid surface 50 of the scapula 52 will now be discussed in detail with reference to FIGS. 8-11. A drill is used to bore the hole 48 through the glenoid surface 50 and into the scapula 52 in a manner known in the art and, thereafter, the anchor peg 40 of the glenoid component 20 is press fit or otherwise interference fit into the hole 48. During installation, the rounded corners 62 and/or side edges 170 between the rounded corners 62 of the square-shaped fins 96 deflect outwardly (or toward an opening of the hole 48), thereby creating an interference with a wall forming the hole that prevents rotational movement of the glenoid component 150 and prevents the glenoid component 20 from moving in a plane perpendicular to the anchor peg 40. While the hole 48 is depicted herein as having a circular cross-section, the hole may optionally have different cross-sections for any of the embodiments disclosed herein, for example, a square-shaped cross section.

Figure 11:
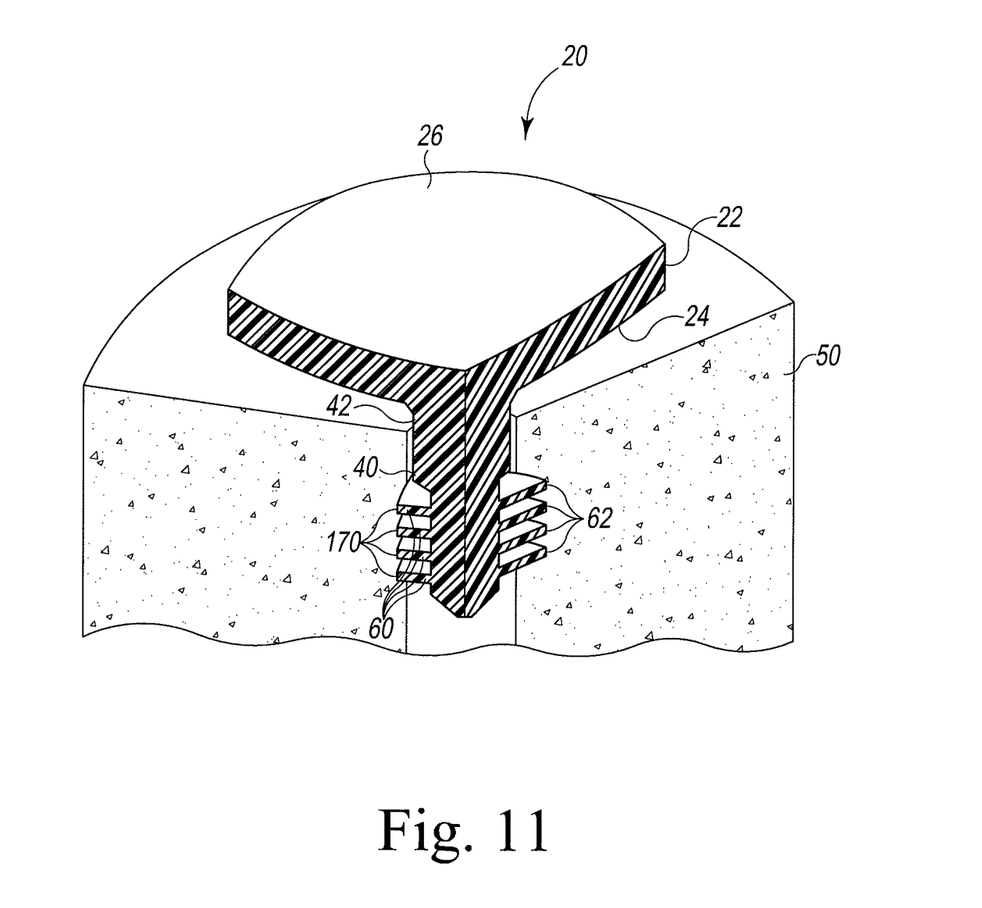
FIG. 11 is a cross-sectional view taken generally along the lines 11-11 of FIG. 9 and depicting a sample level of interference between the fins of the glenoid component of FIGS. 1 and 2 and walls forming the hole formed within the glenoid surface.

As can be seen in FIG. 11, which depicts a range of interference between the fins 60 and a wall forming the hole 48, the square shape of the fins 60 provides a greater interference at the corners 62 of the fins 60 than at the side edges 170 of the fins 96. In one embodiment, an interference between the side edges 170 of the fins 60 and the wall of the hole 48 is between about 0.25 millimeters (mm) and about 2 mm and an interference between the corners 62 of the fins 60 and the wall of the hole 48 is between about 0.5 mm and about 3 mm. In another embodiment, a width of the square fins 60 is greater than a diameter of the hole 48.

Figure 10:
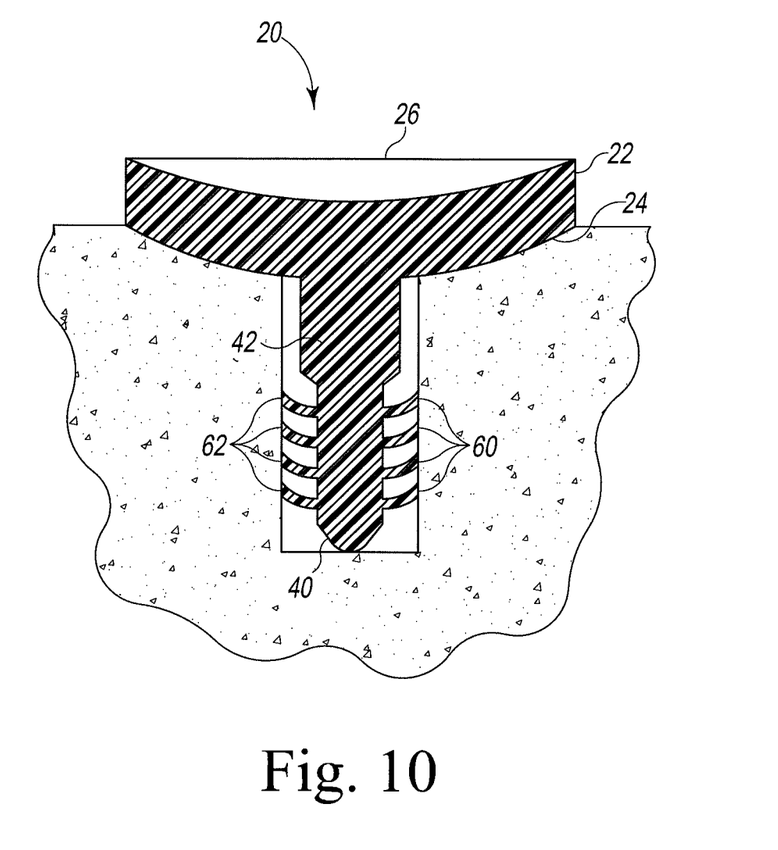
FIG. 10 is a cross-sectional view taken generally along the lines 10-10 of FIG. 9 and depicting deflection of fins of the glenoid component of FIGS. 1 and 2 after securing the glenoid component within the glenoid surface.

The deflection of the fins 60 upon insertion of the glenoid component 20 into the hole 48 is depicted in FIG. 10. In particular, the corners 62 of the fins 60 are deflected outwardly a greater distance than the side edges 170 of the fins 60 are deflected due to the difference in overall interference.

Figure 14:
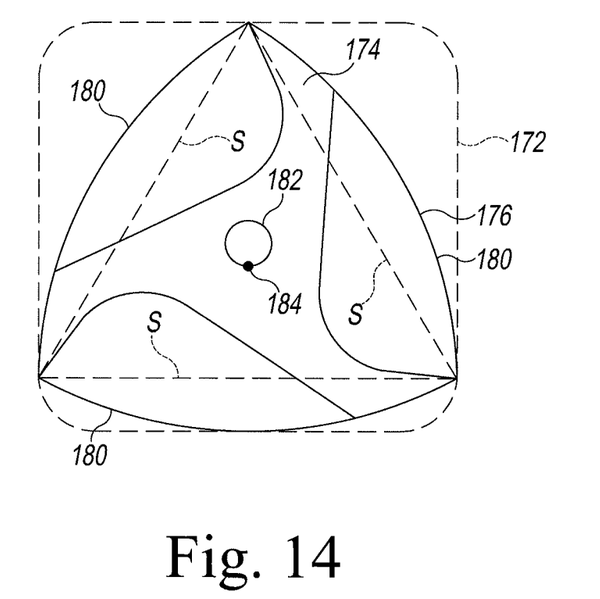
FIG. 14 is a diagrammatic view of an orthopaedic surgical tool having a cutting bit configured to make a square-shaped hole.
Figure 15:
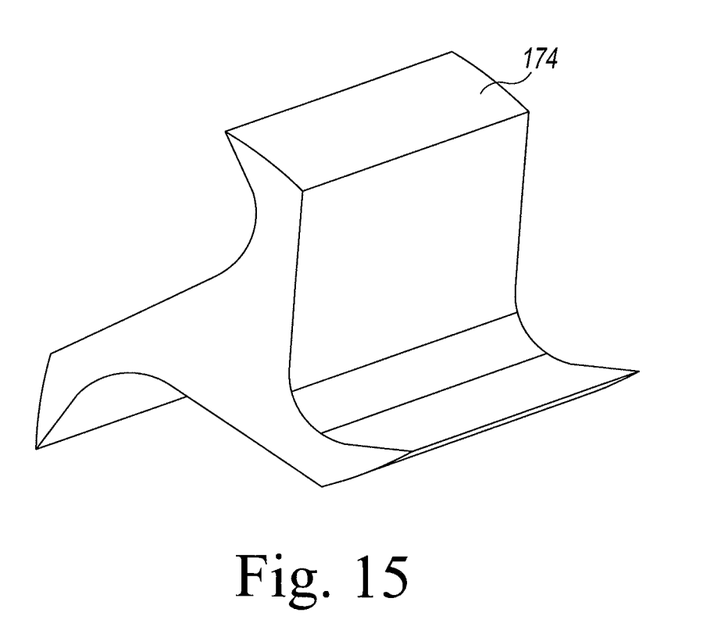
FIG. 15 is a perspective view of the cutting bit of the orthopaedic surgical tool of FIG. 14.

If the hole in which the glenoid component 20 is installed has a square-shaped cross-section, a hole 172 may be be created utilizing a tool having a bit 174 with a general profile of a Reuleux triangle 176, as seen in FIGS. 14 and 15. In particular, a Reuleux triangle 176 is created by starting with an equilateral triangle 178 with sides of length S. With a radius equal to S and a center at a vertice of the triangle 178, three arcs 180 are drawn to form the Reuleux triangle 176. The bit 174, as noted above, has an outer profile that forms the Reuleux triangle 176, such that, when the bit is rotated about a circle 182 starting at a center 184 of the equilateral triangle 178, a square-shaped hole 172 with rounded corners is formed. The glenoid component 20 is secured in the same manner when the hole 172 with a square-shaped cross-section is used. A length of a side of the square forming the fins 96 may be greater than a length of a side of the square forming the hole 172, thereby forming an interference fit. Upon insertion of the gleonid component 20, the rounded corners 62 and the side edges 170 of the fins 96 deflect outwardly (toward an opening of the hole 172). The square shapes would prevent rotation of the glenoid component 20.

Figure 12:
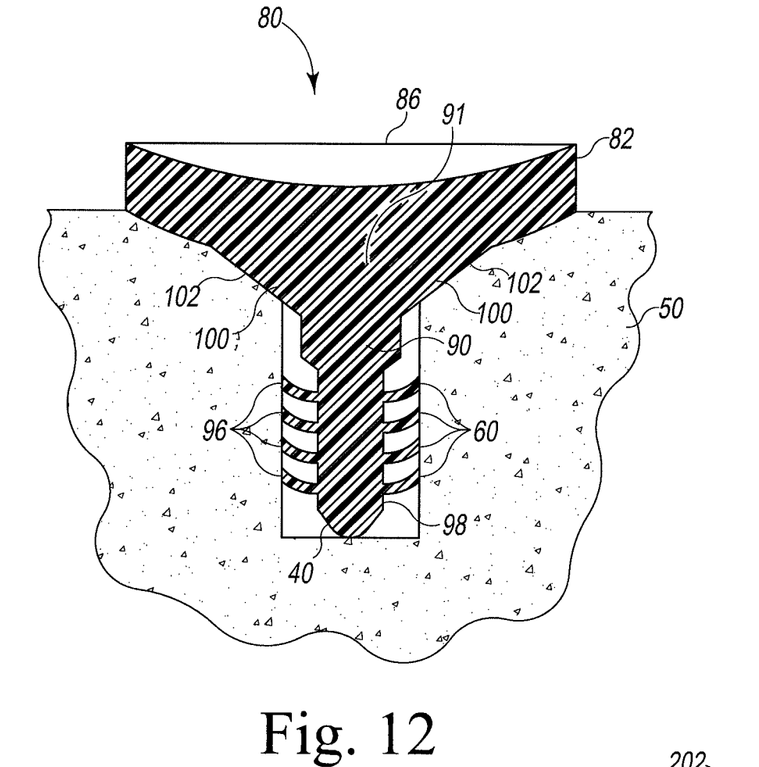
FIG. 12 is a cross-section view similar to that of FIG. 10 and depicting the glenoid component of FIG. 3 secured within the glenoid surface.
Figure 13:
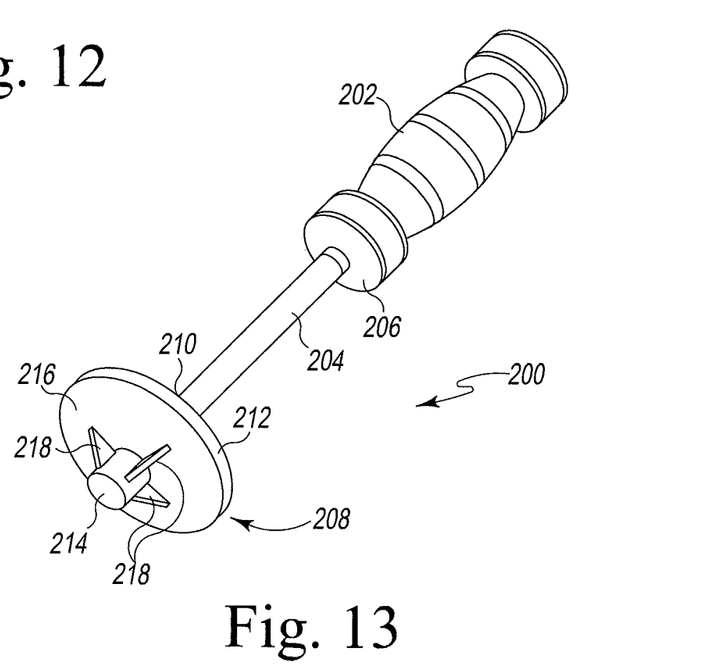
FIG. 13 is a perspective view of a tool that may be used to prepare the glenoid surface prior to securing the glenoid component of FIG. 3 thereto.

Methods of securing the glenoid component 80 of FIGS. 3 and 4 to the glenoid surface 50 of the scapula 52 will now be discussed in detail with reference to FIGS. 12 and 13. A hole 48 is bored into the glenoid surface 50 of the scapula 52 in any manner known in the art. Thereafter, a tool 200 as shown in FIG. 13, may be used to create slots within the glenoid surface 50 surrounding the hole 48. The tool 200 generally includes a handle 202, a rod 204 extending from an end 206 of the handle 202, and a punch 208 attached to an end 210 of the rod 204. The punch 208 includes a plate, for example, a disc 212 having a cylinder 214 extending from a surface 216 of the disc 212 opposite the rod 204. The cylinder 214 is shaped and sized to have a diameter that interferes with the hole 48. In particular, the cylinder 214 has a diameter that is larger than a diameter than the hole 48 and smaller than a diameter of the fins of a glenoid component that fits within the hole 48. Triangular gussets 218 extend outwardly from the cylinder 214. The gussets 218 are similar in size, shape, and number to the gussets 100 of the glenoid component 80. In particular, the gussets 218 are generally orthogonal to the disc 212 and extend outwardly and are generally orthogonal to the cylinder 214. Each gusset 218 is also disposed about 90 degrees around the cylinder 214 from an adjacent gusset 218. Should more or less gussets 100 be formed within a glenoid component, the tool 200 may be modified accordingly.

The tool 200 is grasped by the handle 202, the cylinder 214 of the tool 200 is inserted into the hole 48, and pressure is exerted on the tool 200 toward the glenoid surface 50, thereby creating slots in the glenoid surface 50 corresponding to the gussets 218. The anchor peg 90 of the glenoid component 80 may thereafter be inserted into the hole 48, in the manner described with respect to the first embodiment, until the gussets 218 are disposed within the slots created by the tool 200.

The glenoid component 80 may be secured to the glenoid surface 50 without the use of the tool 200. In such an embodiment, the anchor peg 90 of the glenoid component 80 would be inserted into the hole 48 and the gussets 100 would be driven into the glenoid surface 50, thereby creating the slots in which the gussets 100 are disposed.

The glenoid component 120 of FIG. 5 is secured to the glenoid surface 50 in a manner similar to that of the glenoid component 20 except that a secondary hole is created and, during installation of the glenoid component 120, the stabilizing peg 122 is aligned with and inserted into the secondary hole.

The anchor peg 90 of the glenoid component 150 of FIG. 6 is also secured to the glenoid surface 50 in a manner similar to that of the glenoid component 20. During installation, the cutouts 154 in the fins 152 of the glenoid component 150 allow the fins 152 to deflect outwardly (or toward an opening of the hole 48), thereby creating an interference with a wall forming the hole that prevents rotational movement of the glenoid component 150 and movement of the glenoid component 150 in a plane perpendicular to the glenoid component 150.

The configurations of the fins and/or gussets as shown and described herein eliminate the need for the use of bone cement to secure the anchor peg to the glenoid surface 50 of the scapula 52, thereby reducing the complexity of a typical shoulder replacement procedure.

While the glenoid components shown in the figures and described in detail include have a generally circular configuration, as described above, the principles of the present disclosure may be implemented within a glenoid component having any configuration, for example, oval-shaped. One advantage provided by the glenoid components having a circular configuration is that the glenoid component does not have to be aligned in a specific position or orientation.

As will become apparent from reading the present specification, any of the features of any of the embodiments disclosed herein may be incorporated within any of the other embodiments without departing from the scope of the present disclosure.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure.

The invention claimed is:

1. A glenoid component for securement to a glenoid surface of a scapula so as to provide a bearing surface for a head portion of a humerus, the glenoid component comprising:
   a body portion having (i) a first surface adapted to contact the glenoid surface of a scapula and (ii) a second surface configured to receive the head portion of the humerus; and
   an anchor peg for penetrating the glenoid surface of the scapula so as to secure the body portion to the glenoid surface of the scapula, wherein the anchor peg includes (i) a cylindrical shaft extending from the first surface of the body portion and (ii) a fin secured to and extending outwardly from the cylindrical shaft, the fin being generally square-shaped.

2. The glenoid component of claim 1, further including a plurality of generally square-shaped fins secured to and extending outwardly from the cylindrical shaft of the anchor peg.

3. The glenoid component of claim 2, wherein the generally square-shaped fins have rounded corners.

4. The glenoid component of claim 3, wherein the anchor peg is adapted for insertion into a hole within a glenoid surface of a scapula and wherein the fins have a width that is greater than a width or diameter of a hole in which the anchor peg is inserted and further wherein the fins are configured to prevent rotation of the glenoid component within the glenoid surface.

5. The glenoid component of claim 2, wherein side edges of the fins are configured to have an interference with a wall forming a hole in which the anchor peg is inserted of between about 0.25 millimeters and about 2 millimeters.

6. The glenoid component of claim 5, wherein rounded corners of the fins are configured to have an interference with the wall forming the hole in which the anchor peg is inserted of between about 0.5 millimeters and about 3 millimeters, and wherein the interference between the side walls and the rounded corners with the wall forming the hole prevent rotation of the glenoid component.

7. The glenoid component of claim 2, wherein the anchor peg is configured for insertion into a generally square-shaped hole in the glenoid surface of the scapula.

* * * * *